United States Patent [19]

Renschler et al.

[11] Patent Number: 5,512,435
[45] Date of Patent: Apr. 30, 1996

[54] RECEPTOR-BINDING ANTIPROLIFERATIVE PEPTIDES

[76] Inventors: Markus F. Renschler, 731 Alameda De Las Pulgas, Redwood City, Calif. 94063; Ronald Levy, 966 Mears Ct., Stanford, Calif. 94043; Ramesh R. Bhatt, 777 W. Middlefield #18, Mountain View, Calif. 94025; William J. Dower, 761 Partridge Ave., Menlo Park, Calif. 94025

[21] Appl. No.: 14,426

[22] Filed: Feb. 5, 1993

[51] Int. Cl.$^6$ ............................................. C12Q 1/68
[52] U.S. Cl. .................... 435/6; 435/5; 435/69.1; 435/965; 935/60; 935/80; 935/81; 935/108
[58] Field of Search ................... 435/6, 5, 69.1, 435/965; 935/60, 80, 81, 108

[56] References Cited

U.S. PATENT DOCUMENTS 5,227,159 7/1993 Miller .................................. 424/131.1

FOREIGN PATENT DOCUMENTS

WO91/19818 12/1991 WIPO.
9207574 5/1992 WIPO.
9212996 8/1992 WIPO.

OTHER PUBLICATIONS

George et al., Monoclonal Antibodies Raised Against the Idiotype of the Murine B Cell Lymphoma, BCL$_1$ Act Primarily with Heavy Chain Determinants, Hybridoma 10:219–227 (1991).
Hata et al., Tyrosine Phosphorylaiton of IqM–and IqD–Associated Molecules of a Human B Lymphoma Cell Line B104, International Immunology 4:797–804 (1992).
Lam K.S., Treatment of a B–Cell Lymphoma Using Peptides a Novel Concept, the Western Journal of Medicine 158:475–479 (1993).
Renschler and Levy, Overcoming the Limitations of Chemotherapy in the Treatment of B–Cell Non–Hodgkin's Lymphomas—An Approach Using Radiolabeled Peptide Ligands, the Western Journal of Medicine 158:530–532 (1993).
Smith et al., Production of Heterologous Antibodies Specific for Murine B–Cell Leukemia Immunoglobulin by Immunization with Synthetic Peptides Homologous to Heavy Chain Hypervariable Regions, Cancer Research 45:6119–6123 (1985).
Thielemans et al., Syngeneic Antidiotypic Immune Respones to A B Cell Lymphoma, J. Exp. Med. 162:19–34 (1985).
Levy et al., Therapy of Lymphana Directed at Idio Types, J. Natl Cancer Inst Monographs 10: 61–68, 1990.

*Primary Examiner*—Toni R. Scheiner
*Assistant Examiner*—Donna C. Wortman
*Attorney, Agent, or Firm*—Tracy J. Dunn

[57] ABSTRACT

Methods and composition are provided for identifying antiproliferative polypeptides which inhibit clonal expansion and/or induce apoptosis in cells of a predetermined cell population (e.g., a neoplastic cell sample) expressing a cell surface receptor which is a member of the immunoglobulin superfamily. A predetermined cell population expressing surface immunoglobulin superfamily molecules is isolated from a patient as a cellular sample, such as a lymph node biospy or blood sample containing neoplastic lymphocytic cells. Antiproliferative peptides which are identified by the methods of the invention can be used as therapeutic agents for treating lymphoproliferative disorders by anti-idiotype therapy.

9 Claims, 3 Drawing Sheets

SEQUENCE LISTING ( 1 ) GENERAL INFORMATION:

( i i i ) NUMBER OF SEQUENCES: 65

( 2 ) INFORMATION FOR SEQ ID NO:1:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:1:

```
Lys  Pro  Trp  Tyr  Val  Ser  Arg  Val
 1                    5
```

( 2 ) INFORMATION FOR SEQ ID NO:2:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( i i i ) HYPOTHETICAL: NO ( x i ) SEQUENCE DESCRIPTION: SEQ ID NO:2:

```
CTCTCACTCC  NNKNNKNNKN  NKNNKNNKNN  KNNKGGCGGC  CTGGTTCCGC  GTGGATCCGG     60

CGGCACTGTT  GAAAGTTGT                                                      79
```

( 2 ) INFORMATION FOR SEQ ID NO:3:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i i ) HYPOTHETICAL: NO ( x i ) SEQUENCE DESCRIPTION: SEQ ID NO:3:

```
GGAGTGAGAG  TAGA                                                           14
```

( 2 ) INFORMATION FOR SEQ ID NO:4:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i i ) HYPOTHETICAL: NO ( x i ) SEQUENCE DESCRIPTION: SEQ ID NO:4:

```
CTTTCAACAG  T                                                              11
```

( 2 ) INFORMATION FOR SEQ ID NO:5:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:5:

Gly Gly Leu Arg Arg Ala Ser Leu Gly
1               5

( 2 ) INFORMATION FOR SEQ ID NO:6:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:6:

Lys Pro Trp Tyr Val Ser Arg Val
1               5

( 2 ) INFORMATION FOR SEQ ID NO:7:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:7:

Lys Pro Trp Tyr Val Gly Arg Pro
1               5

( 2 ) INFORMATION FOR SEQ ID NO:8:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:8:

Lys Pro Trp Tyr Val Thr Arg Val
1               5

( 2 ) INFORMATION FOR SEQ ID NO:9:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:9:

Lys Pro Trp Trp Val Thr Arg Val

```
          1               5
```

(2) INFORMATION FOR SEQ ID NO:10:

(i) SEQUENCE CHARACTERISTICS:
        (A) LENGTH: 8 amino acids
        (B) TYPE: amino acid
        (C) STRANDEDNESS: single
        (D) TOPOLOGY: unknown (ii) MOLECULE TYPE: peptide (iii) HYPOTHETICAL: NO (xi) SEQUENCE DESCRIPTION: SEQ ID NO:10:

```
    Lys  Pro  Trp  Trp  Val  Ser  Arg  Val
    1                        5
```

(2) INFORMATION FOR SEQ ID NO:11:

(i) SEQUENCE CHARACTERISTICS:
        (A) LENGTH: 8 amino acids
        (B) TYPE: amino acid
        (C) STRANDEDNESS: single
        (D) TOPOLOGY: unknown (ii) MOLECULE TYPE: peptide (iii) HYPOTHETICAL: NO (xi) SEQUENCE DESCRIPTION: SEQ ID NO:11:

```
    Lys  Pro  Trp  Trp  Val  Val  Arg  Leu
    1                        5
```

(2) INFORMATION FOR SEQ ID NO:12:

(i) SEQUENCE CHARACTERISTICS:
        (A) LENGTH: 8 amino acids
        (B) TYPE: amino acid
        (C) STRANDEDNESS: single
        (D) TOPOLOGY: unknown (ii) MOLECULE TYPE: peptide (iii) HYPOTHETICAL: NO (xi) SEQUENCE DESCRIPTION: SEQ ID NO:12:

```
    Gly  Lys  Pro  Trp  Trp  Ala  Ser  Arg
    1                        5
```

(2) INFORMATION FOR SEQ ID NO:13:

(i) SEQUENCE CHARACTERISTICS:
        (A) LENGTH: 8 amino acids
        (B) TYPE: amino acid
        (C) STRANDEDNESS: single
        (D) TOPOLOGY: unknown (ii) MOLECULE TYPE: peptide (iii) HYPOTHETICAL: NO (xi) SEQUENCE DESCRIPTION: SEQ ID NO:13:

```
    Glu  Lys  Pro  Trp  Trp  Ala  Val  Arg
    1                        5
```

(2) INFORMATION FOR SEQ ID NO:14:

(i) SEQUENCE CHARACTERISTICS:
        (A) LENGTH: 8 amino acids
        (B) TYPE: amino acid (C) STRANDEDNESS: single
(D) TOPOLOGY: unknown (ii) MOLECULE TYPE: peptide (iii) HYPOTHETICAL: NO (xi) SEQUENCE DESCRIPTION: SEQ ID NO:14:

Gly Lys Pro Ile Trp Ala Gly Arg
1               5

(2) INFORMATION FOR SEQ ID NO:15:

(i) SEQUENCE CHARACTERISTICS:
    (A) LENGTH: 8 amino acids
    (B) TYPE: amino acid
    (C) STRANDEDNESS: single
    (D) TOPOLOGY: unknown (ii) MOLECULE TYPE: peptide (iii) HYPOTHETICAL: NO (xi) SEQUENCE DESCRIPTION: SEQ ID NO:15:

Lys Pro Ser Asn Val Ser Arg Val
1               5

(2) INFORMATION FOR SEQ ID NO:16:

(i) SEQUENCE CHARACTERISTICS:
    (A) LENGTH: 8 amino acids
    (B) TYPE: amino acid
    (C) STRANDEDNESS: single
    (D) TOPOLOGY: unknown (ii) MOLECULE TYPE: peptide (iii) HYPOTHETICAL: NO (xi) SEQUENCE DESCRIPTION: SEQ ID NO:16:

Val Pro Trp Tyr Lys Gln Ser Thr
1               5

(2) INFORMATION FOR SEQ ID NO:17:

(i) SEQUENCE CHARACTERISTICS:
    (A) LENGTH: 8 amino acids
    (B) TYPE: amino acid
    (C) STRANDEDNESS: single
    (D) TOPOLOGY: unknown (ii) MOLECULE TYPE: peptide (iii) HYPOTHETICAL: NO (xi) SEQUENCE DESCRIPTION: SEQ ID NO:17:

Ala Pro Trp Tyr Arg Val Ser Pro
1               5

(2) INFORMATION FOR SEQ ID NO:18:

(i) SEQUENCE CHARACTERISTICS:
    (A) LENGTH: 8 amino acids
    (B) TYPE: amino acid
    (C) STRANDEDNESS: single
    (D) TOPOLOGY: unknown (ii) MOLECULE TYPE: peptide (iii) HYPOTHETICAL: NO (xi) SEQUENCE DESCRIPTION: SEQ ID NO:18:

Leu Pro Trp Tyr Leu Tyr Pro Ser
1               5

( 2 ) INFORMATION FOR SEQ ID NO:19:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:19:

Gly Lys Pro Trp Tyr Ala Gly Arg
1               5

( 2 ) INFORMATION FOR SEQ ID NO:20:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:20:

Gln Lys Pro Ile Trp Val Thr Arg
1               5

( 2 ) INFORMATION FOR SEQ ID NO:21:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:21:

Ser Pro Trp Tyr Arg Trp His Asn
1               5

( 2 ) INFORMATION FOR SEQ ID NO:22:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:22:

Lys Asn Gly Pro Trp Tyr Ala Tyr Thr Gly Arg Asp
1               5                   10

( 2 ) INFORMATION FOR SEQ ID NO:23:

( i ) SEQUENCE CHARACTERISTICS:

(A) LENGTH: 8 amino acids
(B) TYPE: amino acid
(C) STRANDEDNESS: single
(D) TOPOLOGY: unknown (ii) MOLECULE TYPE: peptide (iii) HYPOTHETICAL: NO (xi) SEQUENCE DESCRIPTION: SEQ ID NO:23:

```
Lys  Trp  Tyr  Lys  Glu  Arg  Trp  Asn
 1              5
```

(2) INFORMATION FOR SEQ ID NO:24:

(i) SEQUENCE CHARACTERISTICS:
(A) LENGTH: 8 amino acids
(B) TYPE: amino acid
(C) STRANDEDNESS: single
(D) TOPOLOGY: unknown (ii) MOLECULE TYPE: peptide (iii) HYPOTHETICAL: NO (xi) SEQUENCE DESCRIPTION: SEQ ID NO:24:

```
Ser  Trp  Tyr  Asp  Arg  Val  Trp  Asp
 1              5
```

(2) INFORMATION FOR SEQ ID NO:25:

(i) SEQUENCE CHARACTERISTICS:
(A) LENGTH: 8 amino acids
(B) TYPE: amino acid
(C) STRANDEDNESS: single
(D) TOPOLOGY: unknown (ii) MOLECULE TYPE: peptide (iii) HYPOTHETICAL: NO (xi) SEQUENCE DESCRIPTION: SEQ ID NO:25:

```
Leu  Trp  Tyr  Asp  Asp  Pro  Trp  Pro
 1              5
```

(2) INFORMATION FOR SEQ ID NO:26:

(i) SEQUENCE CHARACTERISTICS:
(A) LENGTH: 8 amino acids
(B) TYPE: amino acid
(C) STRANDEDNESS: single
(D) TOPOLOGY: unknown (ii) MOLECULE TYPE: peptide (iii) HYPOTHETICAL: NO (xi) SEQUENCE DESCRIPTION: SEQ ID NO:26:

```
Trp  Trp  Tyr  Asp  Glu  Val  Trp  Gly
 1              5
```

(2) INFORMATION FOR SEQ ID NO:27:

(i) SEQUENCE CHARACTERISTICS:
(A) LENGTH: 8 amino acids
(B) TYPE: amino acid
(C) STRANDEDNESS: single
(D) TOPOLOGY: unknown (ii) MOLECULE TYPE: peptide (iii) HYPOTHETICAL: NO ( x i ) SEQUENCE DESCRIPTION: SEQ ID NO:27:

Ala Trp Phe Asn Glu Met Tyr Val
1               5

( 2 ) INFORMATION FOR SEQ ID NO:28:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:28:

His Trp Tyr Asn Glu Tyr Trp Asp
1               5

( 2 ) INFORMATION FOR SEQ ID NO:29:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:29:

Gly Trp Tyr Asn Glu Thr Trp His
1               5

( 2 ) INFORMATION FOR SEQ ID NO:30:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:30:

Tyr Tyr Cys Ser Pro Trp Cys Asp
1               5

( 2 ) INFORMATION FOR SEQ ID NO:31:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:31:

Ser Trp Tyr Asn Asp Trp Phe Pro
1               5

( 2 ) INFORMATION FOR SEQ ID NO:32:

( i ) SEQUENCE CHARACTERISTICS:
  ( A ) LENGTH: 12 amino acids
  ( B ) TYPE: amino acid
  ( C ) STRANDEDNESS: single
  ( D ) TOPOLOGY: unknown ( i i ) MOLECULE TYPE: peptide ( i i i ) HYPOTHETICAL: NO ( x i ) SEQUENCE DESCRIPTION: SEQ ID NO:32:

Ser Val Pro Pro Ala Trp Gln Ser Arg Val Trp Asn
1               5                   10

( 2 ) INFORMATION FOR SEQ ID NO:33:

( i ) SEQUENCE CHARACTERISTICS:
  ( A ) LENGTH: 10 amino acids
  ( B ) TYPE: amino acid
  ( C ) STRANDEDNESS: single
  ( D ) TOPOLOGY: unknown ( i i ) MOLECULE TYPE: peptide ( i i i ) HYPOTHETICAL: NO ( x i ) SEQUENCE DESCRIPTION: SEQ ID NO:33:

Ser Trp Tyr Asp Gln Val Trp Trp Asp Ser
1               5                   10

( 2 ) INFORMATION FOR SEQ ID NO:34:

( i ) SEQUENCE CHARACTERISTICS:
  ( A ) LENGTH: 12 amino acids
  ( B ) TYPE: amino acid
  ( C ) STRANDEDNESS: single
  ( D ) TOPOLOGY: unknown ( i i ) MOLECULE TYPE: peptide ( i i i ) HYPOTHETICAL: NO ( x i ) SEQUENCE DESCRIPTION: SEQ ID NO:34:

Arg Ser Pro Ser His Trp Tyr Lys Glu Met Trp Asp
1               5                   10

( 2 ) INFORMATION FOR SEQ ID NO:35:

( i ) SEQUENCE CHARACTERISTICS:
  ( A ) LENGTH: 8 amino acids
  ( B ) TYPE: amino acid
  ( C ) STRANDEDNESS: single
  ( D ) TOPOLOGY: unknown ( i i ) MOLECULE TYPE: peptide ( i i i ) HYPOTHETICAL: NO ( x i ) SEQUENCE DESCRIPTION: SEQ ID NO:35:

Gln Val Trp Tyr Lys Trp Pro Asn
1               5

( 2 ) INFORMATION FOR SEQ ID NO:36:

( i ) SEQUENCE CHARACTERISTICS:
  ( A ) LENGTH: 8 amino acids
  ( B ) TYPE: amino acid
  ( C ) STRANDEDNESS: single
  ( D ) TOPOLOGY: unknown ( i i ) MOLECULE TYPE: peptide ( i i i ) HYPOTHETICAL: NO ( x i ) SEQUENCE DESCRIPTION: SEQ ID NO:36:

Ser Pro Trp Tyr Arg Trp His Asn
1               5

( 2 ) INFORMATION FOR SEQ ID NO:37:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:37:

Ile Val Pro Trp Tyr Arg Trp Thr
1               5

( 2 ) INFORMATION FOR SEQ ID NO:38:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:38:

Ala Pro Trp Tyr Arg Val Ser Pro
1               5

( 2 ) INFORMATION FOR SEQ ID NO:39:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:39:

Val Ser Ile Glu Trp Tyr Arg Phe
1               5

( 2 ) INFORMATION FOR SEQ ID NO:40:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:40:

Asp Trp Ala Val Trp Asn Arg Arg
1               5

( 2 ) INFORMATION FOR SEQ ID NO:41:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:41:

Asn Trp Ala Val Trp Thr Lys Arg
    1               5

( 2 ) INFORMATION FOR SEQ ID NO:42:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:42:

Asn Trp Gly Met Trp Ser Lys Arg
    1               5

( 2 ) INFORMATION FOR SEQ ID NO:43:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:43:

Ser Glu Pro Val Asp His Gly Leu
    1               5

( 2 ) INFORMATION FOR SEQ ID NO:44:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:44:

Val Asp Pro Val Asp His Gly Leu
    1               5

( 2 ) INFORMATION FOR SEQ ID NO:45:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:45:

Val Pro Ile Asp His Gly Thr
1               5

( 2 ) INFORMATION FOR SEQ ID NO:46:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:46:

Lys Pro Ala Trp Val Thr Arg Gln
1               5

( 2 ) INFORMATION FOR SEQ ID NO:47:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:47:

Ser Val Pro Pro Ala Trp Gln Ser Arg Val Trp Asn
1               5                   10

( 2 ) INFORMATION FOR SEQ ID NO:48:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:48:

Gly Trp Ser Pro Phe Ile Ala Met
1               5

( 2 ) INFORMATION FOR SEQ ID NO:49:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:49:

Gly Trp Val Pro Phe Ile Ser Leu (2) INFORMATION FOR SEQ ID NO:50:

(i) SEQUENCE CHARACTERISTICS:
        (A) LENGTH: 8 amino acids
        (B) TYPE: amino acid
        (C) STRANDEDNESS: single
        (D) TOPOLOGY: unknown (ii) MOLECULE TYPE: peptide (iii) HYPOTHETICAL: NO (xi) SEQUENCE DESCRIPTION: SEQ ID NO:50:

Tyr  Phe  His  Ser  Met  His  Val  Arg
    1                   5

(2) INFORMATION FOR SEQ ID NO:51:

(i) SEQUENCE CHARACTERISTICS:
        (A) LENGTH: 8 amino acids
        (B) TYPE: amino acid
        (C) STRANDEDNESS: single
        (D) TOPOLOGY: unknown (ii) MOLECULE TYPE: peptide (iii) HYPOTHETICAL: NO (xi) SEQUENCE DESCRIPTION: SEQ ID NO:51:

Phe  His  Asn  Ala  Ser  Gly  Ser  Gly
    1                   5

(2) INFORMATION FOR SEQ ID NO:52:

(i) SEQUENCE CHARACTERISTICS:
        (A) LENGTH: 8 amino acids
        (B) TYPE: amino acid
        (C) STRANDEDNESS: single
        (D) TOPOLOGY: unknown (ii) MOLECULE TYPE: peptide (iii) HYPOTHETICAL: NO (xi) SEQUENCE DESCRIPTION: SEQ ID NO:52:

Tyr  Ser  Phe  Trp  Asp  Leu  Val  Lys
    1                   5

(2) INFORMATION FOR SEQ ID NO:53:

(i) SEQUENCE CHARACTERISTICS:
        (A) LENGTH: 8 amino acids
        (B) TYPE: amino acid
        (C) STRANDEDNESS: single
        (D) TOPOLOGY: unknown (ii) MOLECULE TYPE: peptide (iii) HYPOTHETICAL: NO (xi) SEQUENCE DESCRIPTION: SEQ ID NO:53:

Met  Pro  Glu  Asp  Phe  Tyr  Arg  Arg
    1                   5

(2) INFORMATION FOR SEQ ID NO:54:

(i) SEQUENCE CHARACTERISTICS:
        (A) LENGTH: 8 amino acids
        (B) TYPE: amino acid ( C ) STRANDEDNESS: single
( D ) TOPOLOGY: unknown ( i i ) MOLECULE TYPE: peptide ( i i i ) HYPOTHETICAL: NO ( x i ) SEQUENCE DESCRIPTION: SEQ ID NO:54:

```
Cys  Trp  Thr  Ala  Asp  Cys  Lys  Val
1                   5
```

( 2 ) INFORMATION FOR SEQ ID NO:55:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:55:

```
Gly  Leu  Met  Glu  Met  Val  Arg  Arg
1                   5
```

( 2 ) INFORMATION FOR SEQ ID NO:56:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:56:

```
Tyr  Glu  Met  Pro  Glu  Tyr  Lys  Arg
1                   5
```

( 2 ) INFORMATION FOR SEQ ID NO:57:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:57:

```
Lys  Tyr  Arg  Leu  Cys  Gln  Val  Cys
1                   5
```

( 2 ) INFORMATION FOR SEQ ID NO:58:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:58:

Tyr Val Phe Glu Asp Leu Phe Arg
1               5

( 2 ) INFORMATION FOR SEQ ID NO:59:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:59:

His Trp Ala Ala Leu Met Lys Arg
1               5

( 2 ) INFORMATION FOR SEQ ID NO:60:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:60:

Met Pro Glu Asp Phe Tyr Arg Arg
1               5

( 2 ) INFORMATION FOR SEQ ID NO:61:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:61:

Arg Phe Glu Ser Met Phe Lys Arg
1               5

( 2 ) INFORMATION FOR SEQ ID NO:62:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( x i ) SEQUENCE DESCRIPTION: SEQ ID NO:62:

Tyr Trp Glu Ala His Val Arg Arg
1               5

( 2 ) INFORMATION FOR SEQ ID NO:63:

( i ) SEQUENCE CHARACTERISTICS:

( A ) LENGTH: 8 amino acids
( B ) TYPE: amino acid
( C ) STRANDEDNESS: single
( D ) TOPOLOGY: unknown ( i i ) MOLECULE TYPE: peptide ( i i i ) HYPOTHETICAL: NO ( x i ) SEQUENCE DESCRIPTION: SEQ ID NO:63:

```
Val  Phe  Trp  Gln  Met  Ile  Arg  Arg
1                   5
```

( 2 ) INFORMATION FOR SEQ ID NO:64:

( i ) SEQUENCE CHARACTERISTICS:
( A ) LENGTH: 8 amino acids
( B ) TYPE: amino acid
( C ) STRANDEDNESS: single
( D ) TOPOLOGY: unknown ( i i ) MOLECULE TYPE: peptide ( i i i ) HYPOTHETICAL: NO ( x i ) SEQUENCE DESCRIPTION: SEQ ID NO:64:

```
Met  Pro  Trp  Ala  Met  Phe  Arg  Arg
1                   5
```

( 2 ) INFORMATION FOR SEQ ID NO:65:

( i ) SEQUENCE CHARACTERISTICS:
( A ) LENGTH: 8 amino acids
( B ) TYPE: amino acid
( C ) STRANDEDNESS: single
( D ) TOPOLOGY: unknown ( i i ) MOLECULE TYPE: peptide ( i i i ) HYPOTHETICAL: NO ( x i ) SEQUENCE DESCRIPTION: SEQ ID NO:65:

```
Ser  Phe  Met  Asp  Met  Phe  Lys  Arg
1                   5
```

RECEPTOR-BINDING ANTIPROLIFERATIVE PEPTIDES

This invention was made in the course of work supported by the U.S. Government, which may have certain rights in this invention.

FIELD OF THE INVENTION

The invention provides novel polypeptides which can be used to treat neoplasia, lymphoproliferative diseases, and other pathological states, methods for identifying and administering such peptides or peptidomimetics for therapy and diagnosis of disease, and kits for identifying and producing therapeutic peptides for individual patients.

BACKGROUND

Signalling by membrane immunoglobulin, T cell receptors, and MHC molecules regulate lymphocyte maturation and development. For example, crosslinking of membrane immunoglobulin by antigen or by anti-immunoglobulin antibodies inactivates immature B cells, eliminating many of the B cells capable of producing autoantibodies; whereas crosslinking of membrane immunoglobulin promotes activation of mature B cells for clonal expansion and antibody production against foreign antigens. Activation of protein kinase activity and growth arrest of B cells by crosslinking of membrane immunoglobulin has been reported (Gold et al. (1990) *Nature* 345: 810; Campbell and Sefton (1990) *EMBO J.* 9: 2125). Anti-membrane immunoglobulin antibodies have been reported to exert inhibitory effects on cell proliferation of immature B cells, possibly by inducing programmed cell death, referred to as apoptosis (Benhamou et al. (1990) *Eur. J. Immunol.* 20: 1405). Apoptosis of cytotoxic T lymphocyte clones incubated in the presence of their specific epitopes but not in the presence of irrelevant epitopes has also been reported (Moss et al. (1991) *J. Exp. Med.* 173: 681). Recently, crosslinking of the APO-1 cell surface antigen which is expressed on the surface of activated human T and B lymphocytes has been reported to result in programmed cell death (Oehm et al. (1992) *J. Biol. Chem.* 267: 10709). The PD-1 gene, which is reportedly a member of the immunoglobulin gene superfamily, has been reported to be induced during programmed cell death of both a murine T cell hybridoma and a murine hematopoietic progenitor cell line (Ishida et al. (1992) *EMBO J.* 11: 3887).

Despite these reported findings, rational treatment methods for lymphoproliferative diseases, such as lymphomas and lymphocytic leukemias, are lacking. Currently, conventional combination chemotherapy remains the principal treatment of choice for these disease states. The efficacy of chemotherapy is limited, especially when patients fail first line drug regimens. Other therapy modalities need to be developed to overcome the limitations of chemotherapy. Anti-idiotype antibodies directed against cell surface immunoglobulins of individual lymphocytic neoplasms requires a lengthy and costly process to generate specific anti-idiotype antibodies for each patient individually, as each individual neoplasm likely has a unique idiotype. Moreover, development of anti-idiotype immunoglobulins depends primarily on immunization of nonhuman hosts, such as mice, which yields nonhuman immunoglobulins that are typically immunogenic when administered to humans. The necessity of humanization for therapeutic use of such antibodies would add to the cost and time expenditure, delaying treatment and making individualized anti-idiotype antibody therapy prohibitively expensive. Thus, although anti-idiotype antibodies might theoretically be potential tools for diagnosis and therapy of B cell lymphomas, practical considerations preclude their widespread use in medicine.

Thus there exists a need in the art for methods and compositions for diagnosis and therapy of lymphoproliferative diseases and other diseases of abnormal cell proliferation, including lymphomas and lymphocytic leukemias. It is one object of the invention to provide methods and compositions for diagnosing and treating these pathological conditions, as well as treating immunological conditions which are amenable to targeted anti-proliferative therapy. The present invention fulfills these and other needs.

The references discussed herein are provided solely for their disclosure prior to the filing date of the present application. Nothing herein is to be construed as an admission that the inventors are not entitled to antedate such disclosure by virtue of prior invention.

SUMMARY OF THE INVENTION

In accordance with the foregoing objects, in one aspect of the invention are provided methods for identifying antiproliferative polypeptides which inhibit clonal expansion and/or induce apoptosis in cells of a predetermined cell population (e.g., a neoplastic cell sample) expressing a cell surface receptor which is a member of the immunoglobulin superfamily. A predetermined cell population expressing surface immunoglobulin superfamily molecules is isolated from a patient as a cellular sample, such as a lymph node biopsy or blood sample. The predetermined cell population or its clonal progeny propagated in culture are used as a source of specific surface immunoglobulin superfamily molecules for screening a polypeptide library, such as a bacteriophage peptide display library or a spatially defined polypeptide array on a solid substrate, to determine polypeptide sequences which bind the specific surface immunoglobulin superfamily molecules of the predetermined cell population with an affinity of about at least $1 \times 10^5$ $M^{-1}$ or more, and which substantially lack binding to irrelevant surface immunoglobulin superfamily molecules of other cells, thereby identifying candidate antiproliferative peptide sequences. Peptides and/or peptidomimetics comprising sequences corresponding to or substantially identical to the candidate antiproliferative peptide sequences are assayed, either in native form or crosslinked to additional candidate peptides or peptidomimetics, in cell culture. Such assays determine the biological activity(ies) of the peptide or peptidomimetic species by detecting at least one of the following functional properties: (1) binding to cell surface immunoglobulin superfamily molecules on the predetermined cell population and lacking substantial binding to irrelevant cell populations, (2) inhibition of cell proliferation of the predetermined cell population, (3) induction of apoptosis of the predetermined cell population, (4) stimulation of protein tyrosine kinase activity in the predetermined cell population treated with the peptide or peptidomimetic, (5) modulation of calcium flux across the plasma membrane, and (6) inhibition of other indicia of lymphocyte proliferation in the predetermined cell population but substantially lacking such inhibition in irrelevant cell populations. Biologically active antiproliferative peptides and peptidomimetics are then formulated for administration to a patient having a pathological condition that is characterized by abnormal proliferation of the predetermined cell population, such as a lymphoproliferative disease (e.g., a B cell lymphoma or leukemia).

The invention also provides methods and compositions for identifying and administering anti-idiotype peptides and peptidomimetics for ablating or preventing clonal expansion of lymphocyte subpopulations expressing cell surface immunoglobulin superfamily molecules having specific idiotypes (i.e., antigen or ligand binding clefts). The anti-idiotype peptides and peptidomimetics are administered therapeutically or prophylactically to modulate immune system function by inactivating, by inducing clonal anergy or apoptosis, lymphocyte subpopulations which bind the anti-idiotype molecules.

In one aspect of the invention is provided diagnostic and therapeutic compositions of antiproliferative peptides and peptidomimetics which can be used in therapy and diagnosis of lymphoproliferative diseases in an individual patient. Diagnostic compositions can include imaging conjugates wherein anti-idiotype peptides or peptidomimetics are linked to imaging agents, such as by a covalent linkage or a noncovalent linkage which is substantially nonreleasable under physiological conditions (e.g., a streptavidin-biotin linkage). Therapeutic compositions comprise at least one species of antiproliferative peptide or peptidomimetic for treating lymphoproliferative diseases, other neoplastic conditions, or immune system disorders. Typical therapeutic compositions comprise an effective dosage of a anti-idiotype peptide or peptidomimetic in a pharmaceutically acceptable form, and optionally may include excipients or stabilizers.

The present invention provides compositions of peptides and peptidomimetics that have antiproliferative activity against lymphoma and lymphocytic leukemia cells, and more particularly against B cell lymphomas and B cell lymphocytic leukemias.

The present invention also provide methods for treating or preventing lymphoma and lymphocytic leukemia, and more particularly against B cell lymphomas and B cell lymphocytic leukemias in humans. A therapeutic method for treating a lymphoma or lymphocytic leukemia comprises delivering a therapeutically effective dosage of an antiproliferative peptide to a patient having a lymphoma or lymphocytic leukemia expressing an idiotype which binds the antiproliferative peptide. The method may be used to treat other lymphoproliferative diseases as well. Antiproliferative peptides are non-immunoglobulin proteins and have advantageous pharmacological properties and are relatively inexpensive to identify and manufacture for a patient as compared to anti-idiotype immunoglobulins.

Also provided by the invention is a method for inhibition of the proliferation of lymphoma cells and lymphocytic leukemia cells in culture. The method comprises delivering an antiproliferative dosage of an antiproliferative peptide to a cell culture comprising a lymphoma or lymphocytic leukemia expressing an idiotype which binds the antiproliferative peptide. Such methods will allow identification (and isolation) of variants of lymphoma and lymphocytic leukemia cells which have lost a proliferative phenotype and/or have lost expression of the immunoglobulin superfamily molecule to which the antiproliferative peptide has binding affinity. Such variant cells may be used to screen compounds to identify antineoplastic pharmaceuticals and study the process of neoplastic variability.

Also provided in the invention is a method for inhibiting the proliferation of lymphoma cells or lymphocytic leukemia cells, comprising delivering an inhibitory dose of a non-immunoglobulin antiproliferative peptide which specifically binds to an immunoglobulin superfamily molecule idiotype present on the lymphoma cells or lymphocytic leukemia cells. Such a method can be used to treating a lymphoma or lymphocytic leukemia in a patient, comprising delivering a therapeutically effective dosage of a non-immunoglobulin antiproliferative peptide which specifically binds to an immunoglobulin superfamily molecule idiotype present on the lymphoma cells or lymphocytic leukemia cells.

All publications and patent applications herein are incorporated by reference to the same extent as if each individual publication or patent application was specifically and individually indicated to be incorporated by reference.

Definitions

Figure 1:
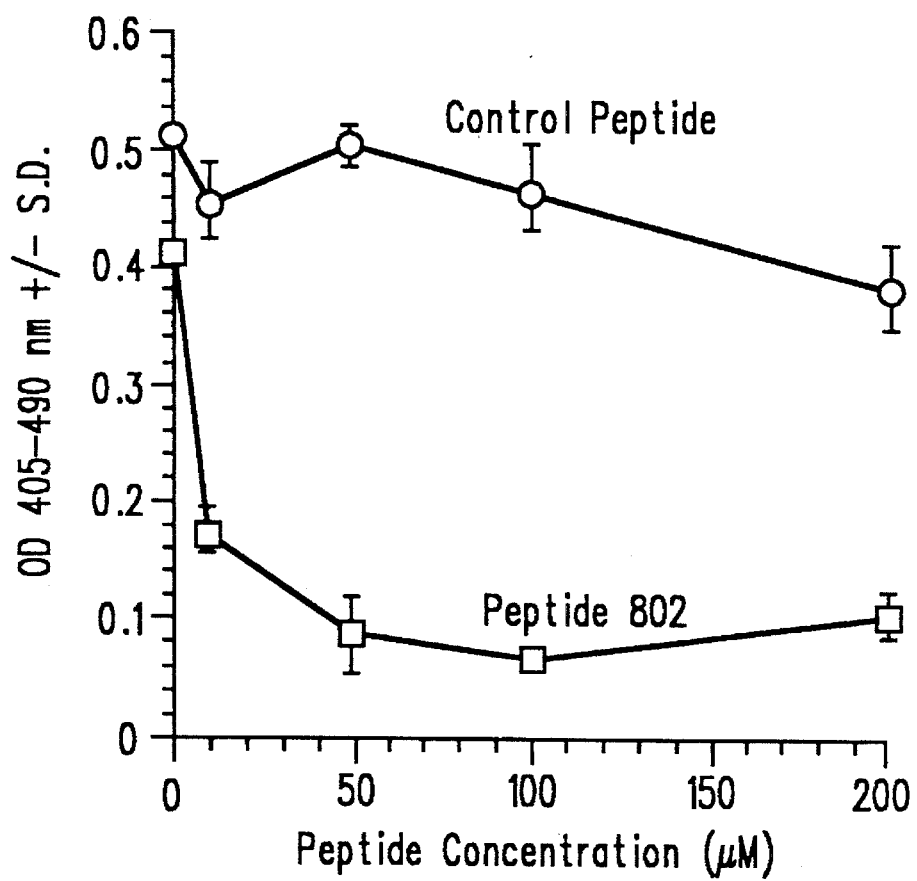
FIG. 1 shows inhibition of anti-idiotype antibody binding to the relevant immunoglobulin with anti-idiotype peptide T802.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

As used herein, the twenty conventional amino acids and their abbreviations follow conventional usage (*Immunology—A Synthesis*, 2nd Edition, E. S. Golub and D. R. Gren, Eds., Sinauer Associates, Sunderland, Mass. (1991), which is incorporated herein by reference). Stereoisomers (e.g., D-amino acids) of the twenty conventional amino acids, unnatural amino acids such as $\alpha,\alpha$-disubstituted amino acids, N-alkyl amino acids, lactic acid, and other unconventional amino acids may also be suitable components for polypeptides of the present invention. Examples of unconventional amino acids include: 4-hydroxyproline, $\gamma$-carboxyglutamate, $\epsilon$-N,N,N-trimethyllysine, $\epsilon$-N-acetyllysine, O-phosphoserine, N-acetylserine, N-formylmethionine, 3-methylhistidine, 5-hydroxylysine, $\omega$-N-methylarginine, and other similar amino acids and imino acids (e.g., 4-hydroxyproline).

As used herein, the term "antiproliferative peptide" refers to a polypeptide that inhibits proliferation or induces apoptosis in a predetermined cell population that expresses a cell surface immunoglobulin superfamily molecule having an idiotype which is substantially absent in other cell populations bearing cell surface immunoglobulin superfamily molecules. Antiproliferative peptides typically have structures and chemical properties defining an epitope which binds to an idiotype-determining binding cleft of an immunoglobulin superfamily molecule, such as a surface IgM or IgD molecule. Antiproliferative peptides are typically polypeptides, although they may comprise D- amino acids in peptide linkage. Alternatively, antiproliferative peptidomimetics comprise polypeptide-like polymers that contain novel backbone structures or unnnatural amino acids (Ellman et al. (1992) *Science* 255: 197, which is incorporated herein by reference), or other non-peptide chemical constituents, including peptoids (Simon et al. (1992) *Proc. Natl. Acad. Sci.* (*U.S.A.*) 89: 9367. Antiproliferative peptides and peptidomimetics generally comprise epitopes which are bound at an idiotype-determining binding cleft (e.g., antigen binding site of an immunoglobulin) and are generally anti-idiotype peptides and peptidomimetics. However, some antiproliferative peptides and peptidomimetics may induce apoptosis, clonal anergy, or proliferative arrest by a mechanism other than binding to an idiotype-determining binding portion of an immunoglobulin superfamily molecule; such antiproliferative peptides may possess the property of inducing apoptosis, clonal anergy, or proliferative arrest in cells bearing immunoglobulin superfamily molecules of various idiotypes.

The term "antineoplastic peptide" is used herein to refer to peptides that have the functional property of inhibiting development or progression of a neoplasm in a human, particularly a lymphoma, lymphocytic leukemia, or preleukemic condition.

The term "candidate antineoplastic peptide" is used herein to refer to a peptide which is identified by one or more screening method(s) of the invention as a putative antineoplastic peptide. Some candidate antineoplastic peptides may have therapeutic potential as anticancer drugs for human use.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes (e.g. $^3H$, $^{14}C$, $^{32}P$, $^{35}S$, $^{125}I$, $^{131}I$), fluorescent labels (e.g., FITC, rhodamine, lanthanide phosphors), enzymatic labels (e.g., horseradish peroxidase, β-galactosidase, luciferase, alkaline phosphatase), biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species.

As used herein "normal blood" or "normal human blood" refers to blood from a healthy human individual who does not have an active neoplastic disease or other disorder of lymphocytic proliferation, or an identified predisposition for developing a neoplastic disease. Similarly, "normal cells", "normal cellular sample", "normal tissue", and "normal lymph node" refers to the respective sample obtained from a healthy human individual who does not have an active neoplastic disease or other lymphoproliferative disorder.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence.

The terms "substantial similarity" or "substantial identity" as used herein denotes a characteristic of a polypeptide sequence or polynucleotide sequence, wherein the polypeptide sequence has at least 50 percent sequence identity compared to a reference sequence, and the nucleic acid sequence has at least 70 percent sequence identity compared to a reference sequence. The percentage of sequence identity is calculated excluding small deletions or additions which total less than 25 percent of the reference sequence. The reference sequence may be a subset of a larger sequence, such as a polypeptide epitope of a larger polypeptide sequence; however, the reference sequence is at least 6 amino residues long in the case of a polypeptide.

As used herein, the terms "biological activity" and "antiproliferative activity" are defined as the capacity to inhibit specifically the proliferation, clonal expansion, or immunologic activation (e.g., production of secreted immunoglobulins) of a predetermined cell population. Thus, an antiproliferative peptide of the invention has biological activity if a predetermined cell population that has been treated with a suitable concentration of the antiproliferative peptide produces a detectable decrease in cell proliferation (e.g., $^3$H-thymidine incorporation, cell number) as compared to a parallel cell culture that is not treated with the antiproliferative peptide and as compared to a cell culture of irrelevant cells (i.e., cells not bearing immunoglobulin superfamily molecules having the same idiotype as the predetermined cell population). Suitable concentrations (i.e., efficacious dose) of antiproliferative peptides and peptidomimetics can be determined by various methods, including generating an empirical dose-response curve, predicting potency and efficacy of a congener by using QSAR methods or molecular modeling, and other methods used in the pharmaceutical sciences (see Fauchere, J. (1986) *Adv. Drug Res.* 15: 29, which is incorporated herein by reference). Antiproliferative peptides of the invention also have specificity for inhibiting proliferation of the predetermined cell population. Thus, a biologically active peptide of the invention specifically inhibits proliferation of one or more predetermined cell populations without producing significant nonspecific cytotoxicity in irrelevant cells. Significant nonspecific cytotoxicity can be determined by various methods, including, for example, determining that treatment of an irrelevant cell culture with an efficacious dose of an agent reduces cell proliferation by at least about 50 percent as compared to a parallel culture that is not treated with the peptide. Other type of assays that can be used to ascertain nonspecific cytotoxicity in cell cultures include: Trypan Blue dye exclusion, incorporation of radiolabeled amino acids and/or radiolabeled nucleotides, mitotic rate (e.g., doubling time), and other methods known in the art.

Polypeptide Nomenclature and Structure Convention

In describing the invention, both single-letter and three-letter abbreviations of the 20 conventional amino acids are used.

The peptide backbone of a polypeptide consists of a repeated sequence of three atoms: the amide N, the α C, and the carbonyl C:

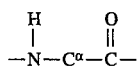

which are generally represented as $N_i$, $C_i^{\alpha}$, and $C_i'$, respectively, where i is the number of the residue, starting from the amino end. In the polypeptide notation used herein, the lefthand direction is the amino terminal direction and the righthand direction is the carboxy-terminal direction, in accordance with standard usage and convention.

An open hyphen at the lefthand end of a peptide sequence indicates that an amino-terminal peptide extension (including unconventional amino acids) may be attached to the amide nitrogen of the leftmost amino acid residue in the given sequence. If there is no open hyphen at the lefthand end of a peptide sequence, that indicates that the leftmost residue is the amino-terminus of the peptide, although the amide nitrogen of the leftmost residue may be chemically modified, for example with an acetyl or methyl group, but typically the amide nitrogen is bonded to the α carbon and hydrogen substituents only.

An open hyphen at the righthand end of a peptide sequence indicates that a carboxy-terminal peptide extension (including unconventional amino acids) may be attached to the carbonyl carbon of the rightmost residue in the given sequence. If there is no open hyphen at the righthand end of a peptide sequence, that indicates that the rightmost residue is the carboxy-terminus of the peptide, although the carbonyl carbon of the rightmost residue may be chemically modified, for example by amidation, but typically the carbonyl carbon is bonded to a hydroxyl group, forming a carboxyl group attached to the α carbon of the rightmost residue.

For example, the sequence -Lys-Pro-Trp- and the carboxy-terminal sequence -Ser-Arg-Val both occur in the octapeptide Lys-Pro-Trp-Tyr-Val-Ser-Arg-Val (SEQ ID NO: 1). However, Lys-Pro-Trp designates a tripeptide since there are no righthand or lefthand open hyphens.

DETAILED DESCRIPTION

Generally, the nomenclature used hereafter and the laboratory procedures in cell culture, molecular genetics, and nucleic acid chemistry and hybridization described below are those well known and commonly employed in the art. Standard techniques are used for recombinant nucleic acid methods, polynucleotide synthesis, polypeptide synthesis, generation and propagation of bacteriophage peptide display libraries and the like and microbial culture and transformation (e.g., electroporation). Generally enzymatic reactions and purification steps are performed according to the manufacturer's specifications. The techniques and procedures are generally performed according to conventional methods in the art and various general references (see, generally, Sambrook et al. Molecular Cloning: A Laboratory Manual, 2d ed. (1989) Cold Spring Harbor Laboratory Press, Cold Spring Harbor, N.Y.; and Antibodies: A Laboratory Manual, (1988) E. Harlow and D. Lane, Cold Spring Harbor Laboratory, Cold Spring Harbor, N.Y., which is incorporated herein by reference) which are provided throughout this document. The procedures therein are believed to be well known in the art and are provided for the convenience of the reader. All the information contained therein is incorporated herein by reference.

The recognized immunoglobulin superfamily is described in The Immunoglobulin Gene Superfamily, A. F. Williams and A. N. Barclay, in Immunoglobulin Genes, T. Honjo, F. W. Alt, and T. H. Rabbitts, eds., (1989) Academic Press: San Diego, Calif., pp.361–387, which is incorporated herein by reference.

Although the methods presented below are described specifically for identifying antiproliferative peptides which bind to immunoglobulin superfamily molecules, it is believed that the method is generally applicable for identifying antiproliferative peptides which bind to non-immunoglobulin cell surface receptors, particularly those receptors which mediate tyrosine kinase activity which is modulatable upon ligand binding.

General Methods

A basis of the present invention is the unexpected finding that peptides having defined sequences can inhibit proliferation, induce clonal anergy, mediate a signal that activates the cell through a tyrosine kinase regulated cell proliferation pathway, and/or induce apoptosis in cells, such as lymphocytic cells of a lymphoma or lymphocytic leukemia, by binding to cell surface immunoglobulin superfamily proteins having specific idiotypes which bind the peptides. Most neoplasms represent a clonal expansion of a single transformed cell, and thus, for example, lymphocytes of any B cell lymphoma generally express a single species of surface immunoglobulin having an idiotype characteristic of that individual B cell lymphoma. For a given individual lymphoma or lymphocytic leukemia it is generally possible to define, by screening libraries of peptides representing a variety of peptide sequences, specific polypeptide sequences which bind to the cell surface immunoglobulin superfamily molecules (e.g., surface IgM or IgD) having the idiotype characteristic of that individual B cell lymphoma. The peptides identified by such screening methods are tested for the ability to inhibit proliferation, induce clonal anergy, modulate tyrosine kinase activity, and/or induce apoptosis in cultured cells of the individual B cell lymphoma, either as individual peptides or as complexes of crosslinked peptides. Peptides which inhibit proliferation, induce clonal anergy, modulate tyrosine kinase activity, and/or induce apoptosis in the cultured lymphoma cells are thereby identified as antiproliferative (or anti-idiotype) peptides and may be administered to a patient which has a B cell lymphoma expressing immunoglobulin superfamily molecules with the characteristic idiotype.

It also has been found that such anti-idiotype peptide screening methods can define multiple peptide sequences which bind to the same immunoglobulin idiotype. By comparison of the multiple anti-idiotype peptide sequences, at least one consensus anti-idiotype peptide sequence motif can be generated which can be used as a sequence template for the generation of additional peptide sequence variants having binding affinity for the immunoglobulin superfamily molecule. Typically, such peptide sequence variants comprise one or two amino acid variations from the anti-idiotype peptide sequence motif, frequently three amino acid variations, and occasionally four or more amino acid variations from the anti-idiotype peptide sequence motif (which may itself comprise alternative residues at specific amino acid positions), and may comprise additional amino acid sequences in polypeptide linkage to the portion containing the consensus motif, either amino-terminal extensions, carboxyterminal extensions, or both. The anti-idiotype peptide consensus motif constitutes a convenient description of the structural and conformational characteristics of peptides which bind to the idiotypic binding site (e.g., the antigen binding site of an immunoglobulin).

In addition to anti-idiotype peptides, a consensus motif may form the basis for synthesis of peptidomimetics. Peptide analogs are commonly used in the pharmaceutical industry as non-peptide drugs with properties analogous to those of the template peptide. These types of non-peptide compound are termed "peptide mimetics" or "peptidomimetics" (Fauchere, J. (1986) *Adv. Drug Res.* 15: 29; Veber and Freidinger (1985) *TINS* p. 392; and Evans et al. (1987) *J. Med. Chem* 30: 1229, which are incorporated herein by reference) and are usually developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biological or pharmacological activity), but have one or more peptide linkages optionally replaced by a linkage selected from the group consisting of: —$CH_2NH$—, —$CH_2S$—, —$CH_2$—$CH_2$—, —CH=CH— (cis and trans), —$COCH_2$—, —$CH(OH)CH_2$—, and —$CH_2SO$—, by methods known in the art and further described in the following references: Spatola, A. F. in "Chemistry and Biochemistry of Amino Acids, Peptides, and Proteins," B. Weinstein, eds , Marcel Dekker, N.Y., p. 267 (1983); Spatola, A. F., Vega Data (March 1983), Vol. 1, Issue 3, "Peptide Backbone Modifications" (general review); Morley, J. S., *Trends Pharm Sci* (1980) pp. 463–468 (general review); Hudson, D. et al., *Int J Pept Prot Res* (1979) 14:177–185 (—$CH_2NH$—, $CH_2CH_2$—); Spatola, A. F. et al., *Life Sci* (1986) 38:1243–1249 (—$CH_2$—S); Hann, M. M., *J Chem Soc Perkin Trans I* (1982) 307–314 (—CH—CH—, cis and trans); Almquist, R. G. et al., *J Med Chem* (1980) 23:1392–1398 (—$COCH_2$—); Jennings-White, C. et al., *Tetrahedron Lett* (1982) 23:2533 (—$COCH_2$—); Szelke, M. et al., European Appln. EP 45665 (1982) CA: 97:39405 (1982) (—$CH(OH)CH_2$—); Holladay, M. W. et al., *Tetrahedron Lett* (1983) 24:4401–4404 (—$C(OH)CH_2$—); and Hruby, V. J., *Life Sci* (1982) 31:189–199 (—$CH_2$—S—); each of which is incorporated herein by reference. A particularly preferred non-peptide linkage is —$CH_2NH$—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) (e.g., immunoglobulin superfamily molecules) to which the peptidomimetic binds to produce the therapeutic effect. Derivitization (e.g., labelling) of peptidomimetics should not substantially interfere with the desired biological or pharmacological activity of the peptidomimetic.

Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch (1992) *Ann. Rev. Biochem.* 61: 387, incorporated herein by reference); for example, by adding internal cysteine residues capable of forming intramolecular disulfide bridges which cyclize the peptide.

Crosslinking of Anti-Idiotype Peptides

It has also been unexpectedly found that crosslinking anti-idiotype peptides, either by linking multiple molecules of a single species of anti-idiotype peptide or by linking multiple species of anti-idiotype peptides, results in enhanced biological activity for inhibiting proliferation, inducing clonal anergy, and/or inducing apoptosis in cells expressing cell surface immunoglobulin superfamily molecules of the characteristic idiotype used for screening the peptide library. Crosslinking is typically accomplished by synthesizing biotinylated anti-idiotype peptides and contacting them with streptavidin under aqueous binding conditions (e.g., buffered physiological saline, optionally including Tween and/or nonspecific blocking protein) to form crosslinked anti-idiotype peptides. Alternatively, anti-idiotype peptides may be crosslinked with a covalent crosslinking agent, such as 1-ethyl-3-(3-dimethylaminopropyl)carbodiimide (Pierce Chemical Co.) or succinimidyl 3-(2-pyridyldithio)propionate (Pierce Chemical Co.) according to methods described in the art (Gilliland et al. (1980) *Proc. Natl. Acad. Sci. (U.S.A.)* 77: 4539; Wu and Wu (1987) *J. Biol. Chem.* 262: 4429; Wu and Wu (1988) *J. Biol. Chem.* 263: 14621; Wu and Wu (1988) *Biochemistry* 27: 887; Wu et al. (1989) *J. Biol. Chem.* 264: 16985; Cotten et al. (1990) *Proc. Natl. Acad. Sci. (U.S.A.)* 87: 4033; Wagner et al. (1990) *Proc. Natl. Acad. Sci. (U.S.A.)* 87: 3410; Zenke et al. (1990) *Proc. Natl. Acad. Sci. (U.S.A.)* 87: 3655; and Wagner et al. (1991) *Proc. Natl. Acad. Sci. (U.S.A.)* 88: 4255, incorporated herein by reference. Peptides can be crosslinked through carboxy-terminal cysteines (e.g., which may be added carboxyterminal to a consensus sequence or substantially identical variant), typically using spacers such as bis-maleimidohexane (BMH) (Pierce Chemical Co.) which can covalently link two sulfhydryl groups. Preferably, crosslinking occurs at non-interfering positions so that substantial biological activity (e.g., antiproliferative activity) is retained. Such non-interfering positions generally are positions that do not form direct contacts with the immunoglobulin superfamily molecule(s) (e.g., surface IgM) to which the peptide or peptidomimetic binds to produce the therapeutic effect.

Alternatively, or in combination with chemical crosslinking, polypeptides consisting essentially of repeats of a peptide consensus sequence (or substantially identical variants thereof) may be linked in peptidyl linkage, typically including a spacer between the repeats comprising a noninterfering amino acid, such as glycine. Such repeat polypeptides can function as a crosslinked complex in inhibiting proliferation, inducing clonal anergy, mediating a signal that activates the cell through a tyrosine kinase regulated cell proliferation pathway, and/or inducing apoptosis in cells.

Identifying Anti-Idiotype Peptides

A predetermined cell population is a population of cells which is substantially comprised of cells that are the clonal progeny of a precursor cell and which express a surface immunoglobulin superfamily molecule having an identical idiotype. For example but not limitation, a biopsy sample of a B cell lymphoma comprises a predetermined cell population since a substantial fraction of the cells in the biopsy sample are derived from a common lymphopoietic precursor cell (i.e., presumably the transformed parent cell) and also express a surface immunoglobulin having essentially identical structure and antigen binding properties (i.e., identical idiotype). It is recognized that some degree of somatic mutation may occur so that minor sequence variations in the immunoglobulin may occur yet not alter idiotypic specificity.

A predetermined cell population comprising cells which express a cell surface immunoglobulin superfamily molecule, such as a T cell receptor ($\alpha/\beta$) or a surface IgM or IgD, is obtained, typically by obtaining a blood sample enriched for a clone of lymphoid cells or lymph node biopsy from a patient suspected of having a lymphoproliferative disease, such as a lymphoma or lymphocytic leukemia (ALL or CLL). The explanted lymphocytic cells may be cultured in a suitable culture medium under growth conditions, may be used directly, or may be used to generate a hybridoma by fusion with an immortalized lymphoid cell line. If the explanted cells are B cells, it is generally preferable to obtain secreted immunoglobulin produced by the cells of hybridomas formed by fusion of the cells with a suitable fusion partner. Alternatively, the predetermined cell population may be used directly for screening. Alternatively, the immunoglobulin superfamily molecule(s) can be recovered from cell lysates or extracts made from the cells, generally via immunoaffinity purification using antibodies directed against the immunoglobulin superfamily molecules (e.g., with an anti-human IgM antibody). For recovery of membrane-bound immunoglobulin superfamily molecules, a mild detergent, such as deoxycholate, may be included to solubilize the molecules.

Immunoglobulin produced by the predetermined cell population (or hybridomas derived therefrom) may be used to screen a peptide library for identifying peptides which bind specifically to the immunoglobulin on the basis of idiotypic identity. Alternatively, the cells of the predetermined cell population may be used to screen a peptide library directly, thereby identifying peptide species which bind to the immunoglobulin superfamily molecule species expressed on the surface of the cells as candidate antiproliferative peptides.

Various embodiments of peptide libraries may be screened to identify anti-idiotype peptides. Two preferred peptide library types are: (1) a bacteriophage peptide display library, which can comprise a bacteriophage antibody display library for selecting anti-idiotype antibodies, and (2) a spatially defined array of peptides fixed to a solid support (U.S. Pat. No. 5,143,854, incorporated herein by reference). Alternative peptide libraries suitable for use have been described in the art, including U.S. Ser. No. 07/963,321; U.S. Ser. No. 07/778,233; and Cull et al. (1992) *Proc. Natl. Acad. Sci. (U.S.A.)* 89:1865, incorporated herein by reference.

Various bacteriophage peptide display libraries are suitable for screening to identify anti-idiotype peptide sequences, including but not limited to those described in PCT/US91/04384; U.S. Ser. No. 07/718,577; U.S. Ser. No. 07/517,659; Cwirla et al. (1990) *Proc. Natl. Acad. Sci. (U.S.A.)* 87: 6378; de la Cruz et al. (1988) *J. Biol. Chem.* 263: 4318; Parmley and Smith, *Gene* 73:305-318 (1988); Scott and Smith (1990) *Science* 249: 386; Devlin et al. (1990) *Science* 249: 404, incorporated herein by reference. Such libraries are screened by a variety of methods, preferably by selective affinity adsorption to a predetermined antigen (e.g., a relevant immunoglobulin or cell of the predetermined cell population).

Various embodiments of bacteriophage antibody display libraries and lambda phage expression libraries have been described (Kang et al. (1991) *Proc. Natl. Acad. Sci. (U.S.A.)* 88: 4363; Clackson et al. (1991) *Nature* 352: 624; McCafferty et al. (1990) *Nature* 348: 552; Burton et al. (1991) *Proc. Natl. Acad. Sci. (U.S.A.)* 88: 10134; Hoogenboom et al. (1991) *Nucleic Acids Res.* 19: 4133; Chang et al. (1991) *J. Immunol.* 147: 3610; Breitling et al. (1991) *Gene* 104: 147; Marks et al. (1991) *J. Mol. Biol.* 222: 581; Barbas et al. (1992) *Proc. Natl. Acad. Sci. (U.S.A.)* 89: 4457; Hawkins and Winter (1992) *J. Immunol.* 22: 867; Marks et al. (1992) *Biotechnology* 10: 779; Marks et al. (1992) *J. Biol. Chem.* 267: 16007; Lowman et al (1991) *Biochemistry* 30: 10832; Lerner et al. (1992) *Science* 258: 1313, incorporated herein by reference). Such antibody display libraries may be used to rapidly identify anti-idiotype antibodies by the methods of the invention.

Typically, the peptide library is screened by contacting the library with cells or the immunoglobulin superfamily molecule from the predetermined cell population under aqueous binding conditions and identifying peptides which bind the cells or immunoglobulin from the predetermined cell type but which substantially do not bind irrelevant cells or immmunoglobulin derived from irrelevant cells. Such peptides are identified as candidate antiproliferative peptides which may be further evaluated for antiproliferative activity by in vitro assays using cultured cells of the predetermined cell population or freshly thawed cells from a biopsy specimen.

For example and not limitation, the following description of a method to identify anti-idiotypic peptides which bind to an immunoglobulin idiotype characteristic of a predetermined cell population by screening a bacteriophage peptide display library is provided. A bacteriophage peptide display library displaying peptide sequences from 6 to 20 amino acids in length (typically as a fusion with a phage coat protein such as pIII of a filamentous bacteriophage) is optionally precleared for non-idiotype-specific binding by contacting the library of bacteriophage particles with an irrelevant class-matched immunoglobulin ,(e.g., a human serum Ig fraction obtained from an individual other than the patient) bound to Sepharose under aqueous binding conditions, and bacteriophage particles bound to the immobilized irrelevant immunoglobulin are removed by separation of the solid phase (e.g., Sepharose). The remaining precleared library is panned over (i.e, contacted with in aqueous binding conditions) irrelevant immunoglobulin coupled to a solid phase (e.g., a plastic Petri plate) and bacteriophage immobilized by binding to the irrelevant immunoglobulin are removed and discarded with the solid phase. The remaining bacteriophage in the supernatant are panned over relevant immunoglobulin (i.e., immunoglobulin derived from the predetermined cell population) immobilized on a solid support and/or immobilized cells of the predetermined cell population (if cells are used, it is preferred that the library is precleared against an equivalent cell type, e.g., a B lymphocyte population). Alternatively, preclearance of the bacteriophage peptide display library may be omitted and the phage population screened directly by panning.

Bacteriophage which do not bind to the immobilized relevant immunoglobulin or immobilized cells remain unbound in the supernatant and are discarded, whereas bacteriophage which are immobilized by specific binding to the relevant immunoglobulin remain bound and are separated from the supernatant by removal of the supernatant and, optionally, rinsing the immobilized fraction with a mild solution (e.g., PBS). Phage displaying peptides without the desired specificity are removed by washing. The degree and stringency of washing required will be determined for each relevant immunoglobulin of interest. A certain degree of control can be exerted over the binding characteristics of the anti-idiotype peptides recovered by adjusting the conditions of the binding incubation and the subsequent washing. The temperature, pH, ionic strength, divalent cations concentration, and the volume and duration of the washing will select for anti-idiotype peptides within particular ranges of affinity for the relevant immunoglobulin. Selection based on slow dissociation rate, which is usually predictive of high affinity, is a practical route. This may be done either by continued incubation in the presence of a saturating amount of a known anti-idiotypic peptide or antibody for the relevant immunoglobulin idiotype, or by increasing the volume, number, and length of the washes. In each case, the rebinding of dissociated peptide-displaying phage is prevented, and with increasing time, peptide-displaying phage of higher and higher affinity are recovered.

Bound bacteriophage are recovered from the immobilized fraction by elution with a known anti-idiotype peptide ligand or with an acidic solution (e.g., pH 2.0 to 2.5), adjusted to neutral pH, and propagated in bacterial hosts to amplify the library of recovered bacteriophage. The recombinant bacteriophage display vectors comprising the displayed peptide which bound to the relevant immunoglobulin are transformed into bacterial cells (e.g. E. coli) wherein they are expressed and phage particles are assembled to form an enriched bacteriophage antibody phage display library.

Such enriched libraries typically are screened further by at least one additional cycle of affinity selection as described above with immobilized relevant immunoglobulin and comprising a low pH (e.g., pH 2.1) elution step. Typically, at least about 2 to 5 cycles of this enrichment procedure (optionally including additional subtractive panning over irrelevant immunoglobulin or cells) are performed and specific anti-idiotype binding clones are isolated.

Once isolated, DNA from the anti-idiotype binding clones is usually prepared and the displayed peptide region sequences are isolated and the nucleotide sequence is determined by sequencing and/or is ligated into a suitable expression vector for high-level expression in bacterial or eukaryotic host cells. The nucleotide sequence of a displayed peptide from a selected clone encodes a putative anti-idiotype peptide. The anti-idiotype peptides thus identified may be used for human therapeutics (e.g., as antiproliferative peptides or toxin conjugates), medical diagnostics (e.g., in vivo imaging of peptide-conjugated imaging agents) and in vitro diagnostic assays (e.g., immunohistochemical staining of histopathological specimens to track recurrence or metastatic disease in a patient).

A variety of techniques can be used in the present invention to diversify a peptide library or to diversify around anti-idiotype peptides found in early rounds of panning to have sufficient binding activity. In one approach, the positive phage (those identified in an early round of panning) are sequenced to determine the identity of the active peptides. Oligonucleotides are then synthesized based on these peptide sequences, employing a low level of all bases incorporated at each step to produce slight variations of the primary oligonucleotide sequences. This mixture of (slightly) degenerate oligonucleotides is then cloned into the affinity phage as described herein. This method produces systematic, controlled variations of the starting peptide sequences. It requires, however, that individual positive phage be sequenced before mutagenesis, and thus is useful for expanding the diversity of small numbers of recovered phage and selecting variants having higher binding affinity and/or higher binding specificity.

Identifying Antiproliferative Peptides

The anti-idiotype peptides identified by screening of a peptide library are thereby identified as candidate antiproliferative peptides. To establish that a candidate antiproliferative peptide possesses antiproliferative activity, the peptide (usually in dimer or higher multimeric form by crosslinking with a linker) is administered to a cell culture containing the predetermined cell population in growth conditions (e.g., RPMI with fetal bovine serum) and the peptide's activity in producing one or more of the following: (1) inhibition of cell proliferation of the predetermined cell population, (2) induction of apoptosis of the predetermined cell population, (3) stimulation of protein tyrosine kinase activity in the predetermined cell population treated with the peptide or peptidomimetic, (4) modulation of calcium flux across the plasma membrane, and (5) inhibition of other indicia of lymphocyte proliferation (e.g., $^3$H-thymidine incorporation) in the predetermined cell population but substantially lacking such inhibition in irrelevant cell populations.

Peptides identified as antiproliferative peptides may be further evaluated by their capacity to reduce tumorigenesis or neoplastic cell burden in nu/nu mice harboring a transplant of the predetermined cell population, as compared to untreated mice harboring an equivalent transplant of the predetermined cell population.

Generally, antiproliferative peptides are at least about 4 amino acids in length, typically at least 5 or 6 amino acids in length, often at least seven or eight amino acids long, and frequently 10 to twelve amino acids long or more. Minimal anti-idiotypic and antiproliferative peptides are often less than 13 amino acids in length, and frequently less than 9 amino acids in length. A frequent size range is from 8 to 12 amino acids, with preferred sizes depending upon the specific idiotypic binding characteristics of the subject relevant immunoglobulin superfamily protein.

Antiproliferative peptides and peptidomimetics which possess antiproliferative activity towards the predetermined cell population may be formulated for therapeutic and diagnostic administration to a patient having a lymphoproliferative disease (e.g., a B cell lymphoma) comprising a clonal expansion of cells having surface immunoglobulin with substantially the same idiotype as the predetermined cell population. Typically, the antiproliferative peptides and peptidomimetics are administered to the patient from whom the predetermined cell population was obtained.

Some antiproliferative peptides may comprise N-terminal and C-terminal additions, generally comprising one or more amino acids in peptide linkage, although non-peptide linkage chemistries (e.g., esterification) and/or chemical modification of the N- and/or C-termini (e.g., C-terminal amidation) may be used. The antiproliferative peptides of the invention possess detectable biological activity as inhibitors of proliferation of the predetermined cell population. It is apparent to those of skill in the art that variation of the precise amino acid sequence of antiproliferative peptides based on consensus anti-idiotype sequence motif(s) will effect the bioavailability, potency, efficacy, half-life, oxidation-resistance, solubility, and other physical, chemical, biological, and pharmacological properties that are relevant to formulating pharmaceutical compositions.

The amino acid sequences of anti-idiotypic peptides identified by the methods of the invention will enable those of skill in the art to produce polypeptides corresponding to the anti-idiotype peptide sequences and sequence variants thereof. Such peptides may be produced in prokaryotic or eukaryotic host cells by expression of polynucleotides encoding an anti-idiotype peptide sequence, frequently as part of a larger polypeptide. Alternatively, such peptides may be synthesized by chemical methods. Methods for expression of heterologous proteins in recombinant hosts, chemical synthesis of polypeptides, and in vitro translation are well known in the art and are described further in Maniatis et al., *Molecular Cloning: A Laboratory Manual* (1989), 2nd Ed., Cold Spring Harbor, N.Y.; Berger and Kimmel, *Methods in Enzymology, Volume* 152, *Guide to Molecular Cloning Techniques* (1987), Academic Press, Inc., San Diego, Calif.; Merrifield, J. (1969) *J. Am. Chem. Soc.* 91: 501; Chaiken I. M. (1981) *CRC Crit. Rev. Biochem.* 11: 255; Kaiser et al.(1989) *Science* 243: 187; Merrifield, B. (1986) *Science* 232: 342; Kent, S. B. H. (1988) *Ann. Rev. Biochem.* 57: 957; and Offord, R. E. (1980) *Semisynthetic Proteins,* Wiley Publishing, which are incorporated herein by reference).

For therapeutic or prophylactic uses, a sterile composition containing a pharmacologically effective dosage of one or more antiproliferative peptide is administered to a human patient or veterinary non-human patient for treatment of a lymphoproliferative condition. Generally, the composition will comprise a anti-idiotype peptide that is identical to or substantially similar to a peptide that binds specifically to the idiotype of a predetermined cell population that is the object of the therapy or prophylaxis. A pharmaceutically acceptable carrier or excipient is often employed in such sterile compositions. Routes of administration are typically intramuscular or intravenous injection or topical application, however some chemical forms of the invention may be effectively administered orally or by other routes. The compositions for parenteral administration will commonly comprise a solution of an antiproliferative peptide or a cocktail thereof dissolved in an acceptable carrier, preferably an aqueous carrier. A variety of aqueous carriers can be used, e.g., water, buffered water, 0.9% saline, 0.3% glycine and the like. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. The concentration of the antiproliferative peptide(s) in these formulations can vary widely, i.e., from less than about 0.01%, usually at least about 0.1% to as much as 5% by weight and will be selected primarily based on fluid volumes, viscosities, etc., in accordance with the particular mode of administration selected.

Thus, a typical pharmaceutical composition for intramuscular injection could be made up to contain 1 ml sterile buffered water, and about 10–1000 mg of antiproliferative peptide. A typical composition for intravenous infusion can be made up to contain 250 ml of sterile Ringer's solution, and about 100–1000 mg of antiproliferative peptide. Actual methods for preparing parenterally administrable compositions will be known or apparent to those skilled in the art and are described in more detail in, for example, *Remington's Pharmaceutical Science,* 15th Ed., Mack Publishing Company, Easton, Pa. (1980), which is incorporated herein by reference. Excipients should be chemically compatible with the peptide(s) or peptidomimetic(s) that are the active ingredient(s) of the preparation, and generally should not increase decomposition, denaturation, or aggregation of active ingredient(s).

The antiproliferative peptides of this invention can be lyophilized for storage and reconstituted in a suitable carrier prior to use. This technique has been shown to be effective with conventional peptides and art-known lyophilization and reconstitution techniques can be employed. It will be appreciated by those skilled in the art that lyophilization and reconstitution can lead to varying degrees of biological activity loss, and that use levels may have to be adjusted to compensate.

The compositions containing the present antiproliferative peptides or cocktails thereof can be administered for prophylactic and/or therapeutic treatments. In therapeutic application, compositions are administered to a patient already affected by the particular lymphoproliferative disease, in an amount sufficient to cure or at least partially arrest the condition and its complications. An amount adequate to accomplish this is defined as a "therapeutically effective dose" or "efficacious dose." Amounts effective for this use will depend upon the severity of the condition, the general state of the patient, and the route of administration, but generally range from about 1 mg to about 2000 mg of antiproliferative peptide per dose, with dosages of from 10 mg to 1000 mg per patient being more commonly used.

In prophylactic applications, compositions containing the antiproliferative peptides or cocktails thereof are administered to a patient not presently in a disease state to enhance the patient's resistance to recurrence or to prolong remission time. Such an amount is defined to be a "prophylactically effective dose." In this use, the precise amounts again depend upon the patient's state of health and general level of immunity, but generally range from 10 mg to 2000 mg per dose, especially 10 to 1000 mg per patient.

Single or multiple administrations of the compositions can be carried out with dose levels and pattern being selected by the treating physician. In any event, the pharmaceutical formulations should provide a quantity of the antiproliferative peptide of this invention sufficient to effectively treat the patient.

Individualized Antiproliferative Peptide Therapy

The methods of the invention are particularly suited to the rapid and inexpensive identification of antiproliferative peptides for treating individual human patients having lymphoma or lymphocytic leukemia. In general, a lymphocyte sample comprising neoplastic lymphocytic cells is obtained from a patient, either as a blood or lymph sample or as a solid tumor biopsy, and used as a source of relevant immunoglobulin (or immunoglobulin superfamily molecule). The relevant immunoglobulin (or immunoglobulin superfamily molecule) is used to screen a peptide library and identify peptides which specifically bind; such peptides (or their substantially identical variants) are assayed for the ability to inhibit proliferation of the patient's neoplastic cells (obtained from a lymphocyte sample from the patient) in cell culture. Such peptides are identified as antiproliferative peptides and are administered to the patient in therapeutically effective dosage(s) for treating the lymphoma or lymphocytic leukemia.

Alternative Embodiments

Optionally, a toxin may be conjugated, typically by covalent linkage, to an anti-idiotype-peptide to deliver a toxic molecule (e.g., ricin, diphtheria toxin, phospholipase) to cells having surface immunoglobulin with substantially the same idiotype as the predetermined cell population.

For diagnostic embodiments, a detection agent such as a label (e.g., biotinyl moieties or FITC) can be linked to an anti-idiotype peptide or peptidomimetic. Similarly, metallothionein, a protein that binds heavy metal atoms, can be linked to, or expressed as a fusion protein with, an anti-idiotype peptide. The resulting product can be used to deliver radionuclides to cells having surface immunoglobulin with substantially the same idiotype as the predetermined cell population for imaging and therapy. Such diagnostic compositions may be used for histopathological diagnosis of neoplasms (e.g., for monitoring chemotherapy efficacy or recurrence of a lymphoma or lymphocytic leukemia) or other applications (e.g., localizing imaging or toxic agents to specific locations in the body for magnetic imaging or radioimaging in vivo or for cytotoxic effect). Such agents may include, for example, a linked component comprising: metals, chemotherapeutic drugs, radiosensitizing agents, cellular toxins, radionuclides, and others. Peptides can be labeled with $^{125}I$ or $^{131}I$ by the Bolton-Hunter method and by chloramine T.

The methods of the invention can be used to identify ligands of peptide-binding cell surface receptors other than members of the immunoglobulin gene superfamily. Such ligands may be antiproliferative peptides, pharmacological antagonists or agonists, or peptides which induce lymphocyte activation. For example, receptors which induce cell activation when antibodies bind to them are candidates for screening peptide libraries to identify peptide ligands which inhibit cell proliferation, induce apoptosis, and/or modulate tyrosine phosphorylation (Ullrich and Schlesinger (1990) *Cell* 61: 203, incorporated herein by reference). The proto-oncogene products her-2/neu (Shepard et al. (1991) *J. Clin. Immunol.* 11: 117; Drebin et al. (1986) *Proc. Natl. Acad. Sci. (U.S.A.)* 83: 9129, incorporated herein by reference) and fas (Itoh et al. (1991) *Cell* 66: 233; Yonehara et al. (1989) *J. Exp. Med.* 169: 1747, incorporated herein by reference) are examples of such receptors. Such methods afford identification of antiproliferative peptides for inhibiting proliferation of lymphoid and non-lymphoid cells, such as neoplastic epithelial cells.

Kits can also be supplied for identifying anti-idiotype peptides which bind a predetermined cell population, such as a lymphoma biopsy sample, obtained from a patient. The kit components generally comprise a peptide library, typically in the form of a bacteriophage peptide display library or solid phase spatially defined peptide array (VLSIPS device), optionally including suitable host cells for propagating a bacteriophage display library, and a suitable aqueous binding buffer. Thus, the components for practicing the methods of the present invention may be provided, usually in a packaged form in a container, either alone or in conjunction with additional reagents. The bacteriophage particles or polynucleotide genomes are typically included in the kits with buffers, such as Tris, phosphate, carbonate, etc., stabilizers, biocides, inert proteins, e.g., serum albumin, or the like, and a set of instructions for use. Typically, such kits will comprise an instruction manual for describing how to perform the screening method and an experimental protocol.

The following examples are offered by way of example and not by way of limitation.

EXPERIMENTAL EXAMPLES

Overview

The immunoglobulin superfamily molecules (e.g., IgM or IgD) of a lymphoma cell line or lymphocytic tumor specimen are produced by fusing the lymphoma cells to murine myeloma cells and screening the hybridomas for the expression of the appropriate light and heavy chains. The immunoglobulins generally are purified from the hybridoma supernatants and used as the relevant immunoglobulin for screening a bacteriophage peptide display library by antibody panning. After four rounds of panning with relevant immunoglobulin, individual bacteriophage colonies were amplified and used in an ELISA with the relevant immunoglobulin to determine the relative or absolute binding affinity for individual selected bacteriophage clones to the relevant immunoglobulino DNA from phage exhibiting high affinity binding to relevant immunoglobulin were sequenced to determine the encoded peptide sequence of the displayed peptide.

Purifying the relevant immunoglobulin

A cell suspension obtained from tumor biopsy specimens or from lymphoma cell lines were isolated as sources of predetermined cell populations. The cell suspensions were mixed with HAT-sensitive heterohybridoma B5 cells. B5 is a heterohybridoma that was generated by the fusion of the NS-1 murine fusion partner (American Type Culture Collection, Rockville, Md.) with a human lymphoma cell. The B5 ,clone has lost the ability to secrete Ig spontaneously. A subclone which retains the ability to secrete Ig when fused to with human B cells. This subclone was made HAT-sensitive by growth in medium containing 8-azaguanine. The mixture of lymphoma cells and B5 cells is exposed to 40% polyethylene glycol and washed with PBS. The cells were plated at a density of $2 \times 10^5$ cells/well in HAT medium into 96-well microtitre plates. The cells were screened by ELISA for secretion of immunoglobulins of the same light chain class as the lymphoma. The highest producing clones are expanded to larger culture volumes. The supernatants of the hybridomas are pooled and run through protein A columns (for IgG-secreting hybridomas) or a Sepharose column coated with a monoclonal anti-IgM antibody (for IgM-secreting hybridomas). The Ig is eluted from the column with glycine-HCl and dialyzed overnight in PBS. The resultant dialyzed Ig constitutes relevant immunoglobulin with respect to the predetermined cell population used to generate it. A relevant immunoglobulin from a B cell lymphoma of a patient was so prepared and used to screen three bacteriophage peptide display libraries. The cell line was identified and designated Sup B8 which expresses a monoclonal immunoglobulin designated as the Tab idiotype; the Tab monoclonal was used to screen peptide libraries to identify anti-idiotype peptides.

Filamentous phage display libraries

The vector pAFF1 and the libraries used are available from Affymax, Palo Alto, Calif. A description of the construction of one of the libraries follows: The vector has two BstXI sites at the 5' region of gene III. The vector is cut with BstXI and cut vector is purified. A collection of oligonucleotides encoding all possible octapeptides with the sequence 5'C TCT CAC TCC (NNK)$^8$ GGC GGC CTG GTT CCG CGT GGA TCC GGC GGC ACT GTT GAA AGT TGT 3' (SEQ ID NO: 2) in which N stands for equimolar A, C, G, and T, and K stands for equimolar ratios of G or T, is annealed to two "half-site" oligonucleotides with the sequences 5'-GGA GTG AGA GTA GA-3' (SEQ ID NO: 3) and 5'-CTT TCA ACA GT-3' (SEQ ID NO: 4) and ligated into the vector by the addition of ligase and ATP. The single stranded gaps are filled in with Klenow DNA polymerase. The DNA is electroporated into E. coli MC1061 in multiple batches. The eletrotransformations are pooled and grown in selective media through 10 doublings. The phage are isolated by clearing the supernatant from the bacteria by centrifugation, followed by precipitation of the phage by polyethylene glycol. The phage were plated out on LB-tetracycline plates to determine the titer of infectious particles.

Identifying ligands with high affinity with the immunoglobulin receptor

The purified Ig's were immobilized on plastic plates or sepharose columns. Approximately $10^{11}$ to $10^{12}$ infectious phage are incubated with the Ig. The plates or the column is washed with a wash buffer. Adherent phage are eluded with glycine-HC1. Eluted phage are amplified by infecting logarithmic E. coli K91 and growing them in selective media overnight. The phage were isolated from the plates, separated from the bacteria, purified by polyethylene glycol precipitation, resuspended, and amplified. The affinity purification step was repeated four times. After the final round, E. coli is infected with the phage and plated at low density. Individual colonies were picked and amplified in E. coli overnight. Phage were purified from bacterial supernatant. A phage ELISA was performed on the amplified individual phage to determine the binding to the given immunoglobulin immobilized on the ELISA plate. The genomes of those phage which preferentially bound to the relevant immunoglobulin were sequenced. Single stranded DNA was prepared from the phage and sequenced with a primer complementary to the sequence of gene III, 15 nucleotides to the 3' side of the BstXI site using the chain-termination DNA sequencing method. A peptide with the amino acid sequence corresponding to a common nucleotide sequence of phage obtained from affinity purification was made synthetically and purified by HPLC. A variant peptide elongated at the carboxy-terminus by the amino acid sequence G-G-L-R-R-A-S-L-G, (SEQ ID NO: 5) the substrate for cAMP-dependent protein kinase, was also synthesized. The affinity constant of the peptide ligand is determined with soluble radioimmunoassay using the $^{32}$p labeled variant peptide and the purified Ig. FIG. 1 shows inhibition of anti-idiotype antibody binding to the relevent immunoglobulin with anti-idiotype peptide 3T802 with an $IC_{50}$ of between 1 and 10 µM. Immunoglobulin of the Tab idiotype was plated on 96-well microtitre plates and detected with murine monoclonal anti-idiotype antibody in an ELISA format and the ability of the peptide to inhibit binding of the anti-idiotype monoclonal to Tab was measured. Binding was measured with peptide added prior to the addition of the anti-idiotype antibody.

Figure 2:
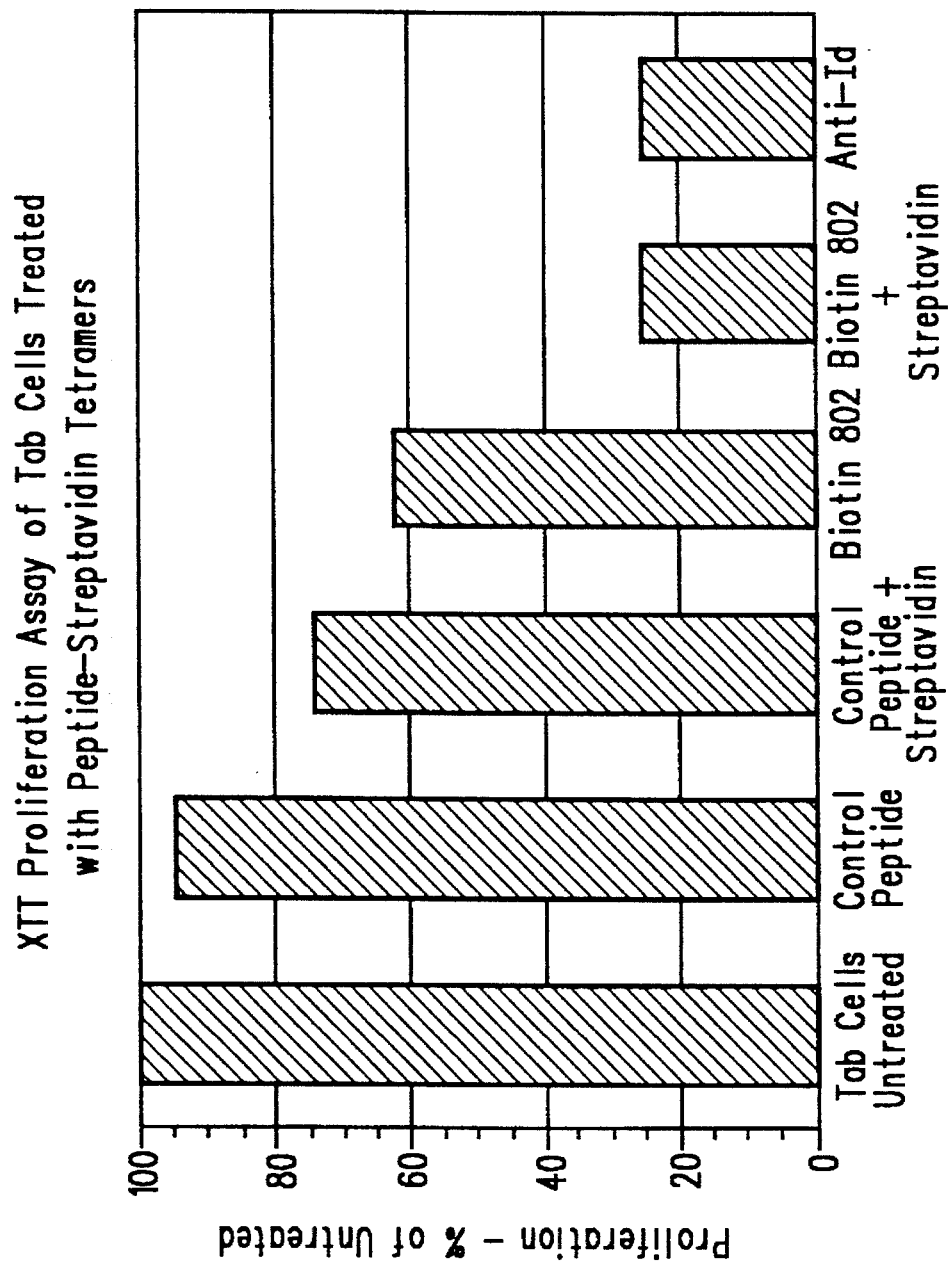
FIG. 2 shows the antiproliferative effect of biotinylated peptide 3T802 conjugated to streptavidin.

Proliferation assays of lymphoma cells with and without ligand were performed in 96 well tissue culture plates. 5,000 to 10,000 tumor cells per well are plated in 100 µl complete medium. Peptides, biotinylated peptides, biotinylated peptides with streptavidin were reconstituted in 100 µl of medium and added to the wells. The cells were incubated for 3 days at 37 degrees Celsius. XTT assays (Jost et al. (1992) J. Immunol. Meth. 147: 153, incorporated herein by reference) were performed to quantitate the number of cells proliferating at that time. FIG. 2 shows the antiproliferative effect of biotinylated peptide 3T802 conjugated to streptavidin. In a three day proliferation assay, approximately 5,000 Tab lymphoma cells were plated on complete medium mixed with peptides in 96-well culture plates. After three days, an XTT assay was performed measuring the number of metabolically active cells. Data is presented as averages from five samples in each group.

An alternate method for quantitation of proliferation is $^3$H-thymidine incorporation assays. $^3$H-thymidine is added 24 hours before cell harvest, followed by cell harvest onto glass fiber filters and determination of incorporated radioactivity with a liquid scintillation counter.

Immunoblots were used to evaluate the stimulation of protein tyrosine phosphorylation by ligand binding. Cells growing at mid-log phase are washed in fresh medium. About 2 million cells are reconstituted in 1 ml medium. Anti-IgM antibodies or peptides are added for various time periods. Phosphorylation is then inhibited with a buffer containing 1 mM sodium orthovanadate in PBS. The cells are lysed. The lysates are run on an SDS-polyacrylamide gel and subsequently transferred to nitrocellulose. Phosphorylated tyrosine are detected with a monoclonal anti-phosphotyrosine antibody.

Antiproliferative peptides

Figure 3:
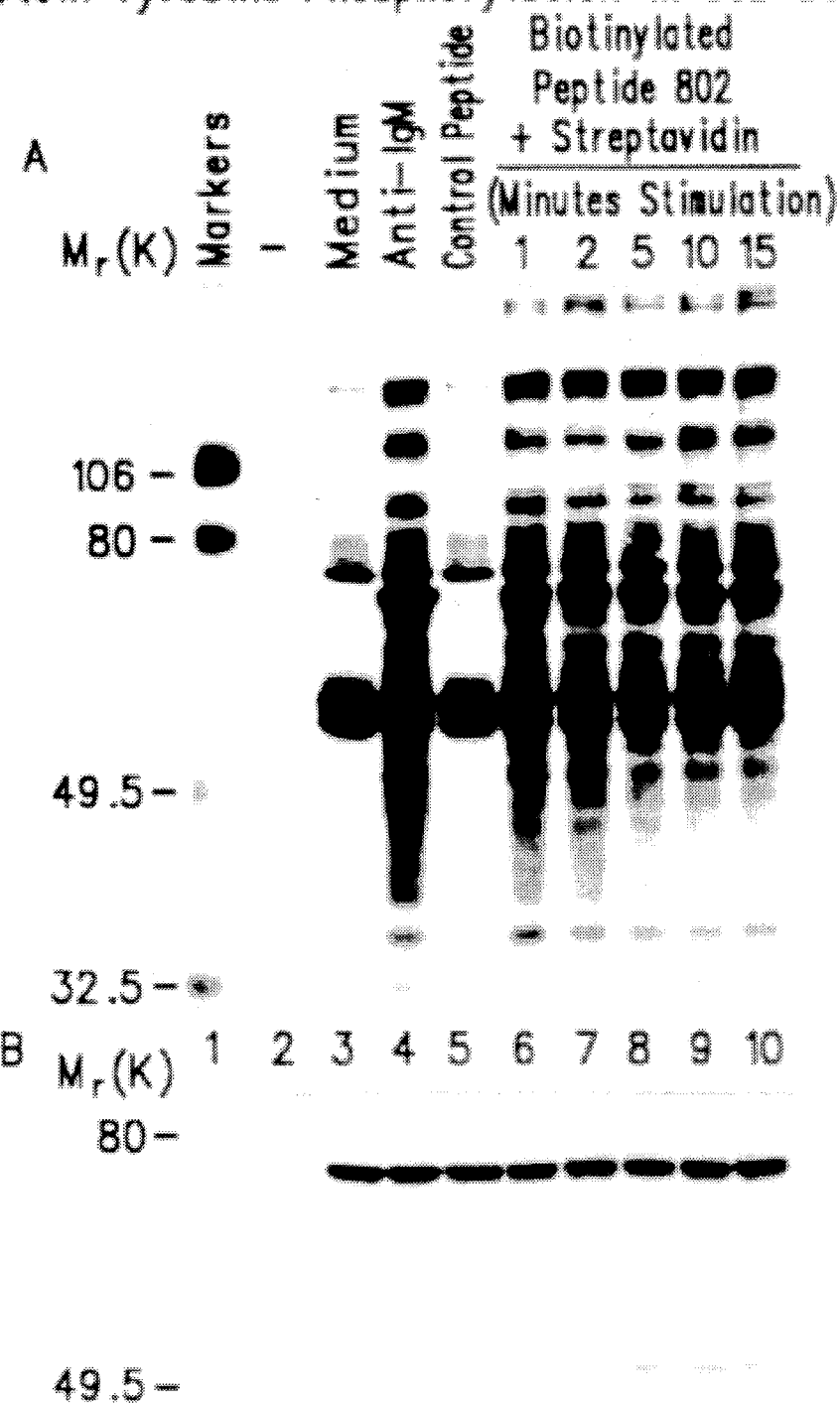
FIG. 3 shows a Western blot showing tyrosine phosphorylation in SupB8 (Tab) cells.

The relevant immunoglobulin from a B cell lymphoma of a human patient was used to screen three bacteriophage display libraries. The amino acid sequences of about at least 60 positive phage which bound to the relevant immunoglobulin were identified by sequencing the peptide display portion of the pIII gene of the selected phage. Several of the peptides were produced by chemical synthesis. The peptides were determined to bind to immunoglobulin of the predetermined cell population (B cell lymphoma) obtained from the patient but not to those of other B lymphocytic cell types tested. The anti-idiotype peptides were biotinylated and linked with streptavidin by allowing 50 µM streptavidin reconstituted in RPMI to react with 200 µM biotinylated anti-idiotype peptide in a 1:1 mixture over 30 minutes at room temperature to produce a tetramer of four peptides conjugated to a streptavidin molecule and was shown to inhibit the growth of the predetermined cell population (i.e., a cell line established from the patient's B cell lymphoma cells) but not other B lymphocytic cell lines with different idiotypes. The anti-idiotype peptide streptavidin complex induced tyrosine kinase activity in the cell line established from the patient's B cell lymphoma cells but not in other B lymphocytic cell lines with different idiotypes. FIG. 3 shows a Westernblot showing tyrosine phosphorylation in SupB8 (Tab) cells. Approximately $2\times10^6$ SupB8 (Tab) cells were stimulated with peptides (10 µM) or antibodies. After 2 minutes or the times shown in FIG. 3, cells were washed in buffer containing orthovanadate to inhibit phosphorylation. Cell lysates were electrophoresed using an 8% SDS-PAGE and transferred to nitrocellulose. In panel (A), phosphorylated tyrosines were detected with a murine anti-phosphotyrosine antibody and visualized with a goat anti-mouse IgG antibody conjugated to horseradish peroxidase. In panel (B), detection with the goat anti-mouse IgG antibody coupled to horseradish peroxidase alone, showing equal loading in all lanes. The blot shows active phosphorylation with the anti-idiotype peptide (lanes 6–10) as early as 1 minute after stimulation, but not with a control peptide-streptavidin complex (lane 5).

Table I shows amino acid sequences of some of the peptides identified and shown to bind the idiotype of the patient's B cell lymphoma.

TABLE I

TABLE 1: Amino acid sequences of some of the peptides found to bind to the immunoglobulin receptor tested

| Sample-ID | Sequence |
|---|---|
| AMR401 | K—P—W—Y—V—S—R—V (SEQ ID NO: 6) |
| A4R02 | K—P—W—Y—V—G—R—P (SEQ ID NO: 7) |
| A4RO9 | K—P—W—Y—V—T—R—V (SEQ ID NO: 8) |
| A3T813 | K—P—W—W—V—T—R—V (SEQ ID NO: 9) |
| A3T802 | K—P—W—W—V—S—R—V (SEQ ID NO: 10) |
| A4R07 | K—P—W—W—V—V—R—L (SEQ ID NO: 11) |
| AMR311 | G—K—P—W—W—A—S—R (SEQ ID NO: 12) |
| A4R14 | E—K—P—W—W—A—V—R (SEQ ID NO: 13) |
| AMR304 | G—K—P—I—W—A—G—R (SEQ ID NO: 14) |
| AMR421 | K—P—S—N—V—S—R—V (SEQ ID NO: 15) |
| AMR426 | V—P—W—Y—K—Q—S—T (SEQ ID NO: 16) |
| AMR430 | A—P—W—Y—R—V—S—P (SEQ ID NO: 17) |
| AMR440 | L—P—W—Y—L—Y—P—S (SEQ ID NO: 18) |
| AMR442, 446 | G—K—P—W—Y—A—G—R (SEQ ID NO: 19) |
| A3T821 | Q—K—P—I—W—V—T—R (SEQ ID NO: 20) |
| AMR416 | S—P—W—Y—R—W—H—N (SEQ ID NO: 21) |
| A3T1204 | K—N—G—P—W—Y—A—Y—T—G—R—D (SEQ ID NO: 22) |
| AMR432, 35 | K—W—Y—K—E—R—W—N (SEQ ID NO: 23) |
| AMR402 | S—W—Y—D—R—V—W—D (SEQ ID NO: 24) |
| AMR411 | L—W—Y—D—D—P—W—P (SEQ ID NO: 25) |
| AMR408 | W—W—Y—D—E—V—W—G (SEQ ID NO: 26) |
| AMR412 | A—W—F—N—E—M—Y—V (SEQ ID NO: 27) |
| AMR431 | H—W—Y—N—E—Y—W—D (SEQ ID NO: 28) |
| AMR418 | G—W—Y—N—E—T—W—H (SEQ ID NO: 29) |
| AMR422, 23, 28 3 | Y—Y—C—S—P—W—C—D (SEQ ID NO: 30) |
| AMR307 | S—W—Y—N—D—W—F—P (SEQ ID NO: 31) |
| A3T1206 | S—V—P—P—A—W—Q—S—R—V—W—N (SEQ ID NO: 32) |
| A3T1220 | S—W—Y—D—Q—V—W—W—D—S (SEQ ID NO: 33) |
| A3T1217 | R—S—P—S—H—W—Y—K—E—M—W—D (SEQ ID NO: 34) |
| AMR427 | Q—V—W—Y—K—W—P—N (SEQ ID NO: 35) |
| AMR416 | S—P—W—Y—R—W—H—N (SEQ ID NO: 36) |
| AMR444 | I—V—P—W—Y—R—W—T (SEQ ID NO: 37) |
| AMR430 | A—P—W—Y—R—V—S—P (SEQ ID NO: 38) |
| AMR413 | V—S—I—E—W—Y—R—F (SEQ ID NO: 39) |
| AT812 | D—W—A—V—W—N—R—R (SEQ ID NO: 40) |
| A4R01 | N—W—A—V—W—T—K—R (SEQ ID NO: 41) |
| AT817 | N—W—G—M—W—S—K—R (SEQ ID NO: 42) |
| AT807 | S—E—P—V—D—H—G—L (SEQ ID NO: 43) |
| AT811 | V—D—P—V—D—H—G—L (SEQ ID NO: 44) |
| AT819 | V—P—I—D—H—G—T (SEQ ID NO: 45) |
| A4R16 | K—P—A—W—V—T—R—Q (SEQ ID NO: 46) |
| A1206 | S—V—P—P—A—W—Q—S—R—V—W—N (SEQ ID NO: 47) |
| AT807 | G—W—S—P—F—I—A—M (SEQ ID NO: 48) |
| A4811 | G—W—V—P—F—I—S—L (SEQ ID NO: 49) |
| AMR436 | Y—F—H—S—M—H—V—R (SEQ ID NO: 50) |
| AMR305 | F—H—N—A—S—G—S—G (SEQ ID NO: 51) |
| AT801 | Y—S—F—W—D—L—V—K (SEQ ID NO: 52) |
| AT804 | M—P—E—D—F—Y—R—R (SEQ ID NO: 53) |
| AT805 | C—W—T—A—D—C—K—V (SEQ ID NO: 54) |
| AT808 | G—L—M—E—M—V—R—R (SEQ ID NO: 55) |
| AT809 | Y—E—M—P—E—Y—K—R (SEQ ID NO: 56) |
| AT810 | K—Y—R—L—C—Q—V—C (SEQ ID NO: 57) |
| AT816 | Y—V—F—E—D—L—F—R (SEQ ID NO: 58) |
| AT822 | H—W—A—A—L—M—K—R (SEQ ID NO: 59) |
| A4R03 | M—P—E—D—F—Y—R—R (SEQ ID NO: 60) |
| A4R06 | R—F—E—S—M—F—K—R (SEQ ID NO: 61) |
| A4R10 | Y—W—E—A—H—V—R—R (SEQ ID NO: 62) |
| A4L09 | V—F—W—Q—M—I—R—R (SEQ ID NO: 63) |
| A4L19 | M—P—W—A—M—F—R—R (SEQ ID NO: 64) |
| A4L29 | S—F—M—D—M—F—K—R (SEQ ID NO: 65) |

Although the present invention has been described in some detail by way of illustration for purposes of clarity of understanding, it will be apparent that certain changes and modifications may be practiced within the scope of the claims.

We claim:

1. A method for identifying antiproliferative peptides, comprising the steps of:

obtaining a predetermined cell population from a patient, wherein said predetermined cell population comprises cells expressing on their extracellular surface an immunoglobulin superfamily species having a single idiotype characteristic to the predetermined cell population;

contacting under aqueous binding conditions said immunoglobulin superfamily species to a peptide library comprising a multiplicity of peptide library members having distinct peptide sequences;

identifying a peptide library member that binds specifically to said immunoglobulin superfamily species idiotype as an anti-idiotype peptide;

contacting under growth conditions said anti-idiotype peptide to said predetermined cell population or their clonal progeny and measuring an indicator of cell proliferation or activation in the predetermined cell population; and identifying an anti-idiotype peptide which inhibits cell proliferation of the predetermined cell population as an antiproliferative peptide.

2. A method according to claim 1, comprising the further step of determining the amino acid sequence of said anti-idiotype peptide.

3. A method according to claim 1, wherein the peptide library is a bacteriophage display library comprising a multiplicity of bacteriophage species having sequences of said peptide library members displayed as fusion proteins with a coat protein of the bacteriophage.

4. A method according to claim 1, wherein the immunoglobulin superfamily species is an immunoglobulin expressed by a B cell lymphocytic cell population.

5. A method according to claim 4, wherein said B cell lymphocytic cell population is a human B cell lymphoma.

6. A method according to claim 1, wherein the indicator of cell proliferation is tyrosine phosphorylation of polypeptides.

7. A method of claim 1, wherein the anti-idiotype peptide is a peptide sequence selected from the group of peptides consisting of:

K—P—W—Y—V—S—R—V; K—P—W—Y—V—G—R—P; K—P—W—Y—V—T—R—V;
K—P—W—W—V—T—R—V; K—P—W—W—V—S—R—V; K—P—W—W—V—V R—L;
G—K—P—W—W—A—S—R; E—K—P—W—W—A—V—R; G—K—P—I—W—A—G—R;
K—P—S—N—V—S—R—V; V—P—W—Y—K—O—S—T; A—P—W—Y—R—V—S—P;
L—P—W—Y—L—Y—P—S; G—K—P—W—Y—A—G—R; O—K—P—I—W—V—T—R;
S—P—W—Y—R—W—H—N; K—N—G—P—W—Y—A—Y—T—G—R—D;
K—W—Y—K—E—R—W—N;
S—W—Y—D—R—V—W—D; L—W—Y—D—D—P—W—P; W—W—Y—D—E—V—W—G;
A—W—F—N—E—M—Y—V; H—W—Y—N—E—Y—W—D; G—W—Y—N—E—T—W—H;
Y—Y—C—S—P—W—C—D; S—W—Y—N—D—W—F—P;
S—V—P—P—A—W—O—S—R—V—W—N;
S—W—Y—D—O—V—W—W—D—S; R—S—P—S—H—W—Y—K—E—M—W—D;
O—V—W—Y—K—W—P—N;
S—P—W—Y—R—W—H—N; I—V—P—W—Y—R—W—T; A—P—W—Y—R—V—S—P;
V—S—I—E—W—Y—R—F; D—W—A—V—W—N—R—R; N—W—A—V—W—T—K—R;
N—W—G—M—W—S—K—R; S—E—P—V—D—H—G—L; V—D—P—V—D—H—G—L;
V—P—I—D—H—G—T; K—P—A—W—V—T—R—O;
S—V—P—P—A—W—O—S—R—V—W—N;
G—W—S—P—F—I—A—M; G—W—V—P—F—I—S—L; Y—F—H—S—M—H—V—R;
F—H—N—A—S—G—S—G; Y—S—F—W—D—L—V—K; M—P—E—D—F—Y—R—R;
C—W—T—A—D—C—K—V; G—L—M—E—M—V—R—R; Y—E—M—P—E—Y—K—R;
K—Y—R—L—C—O—V—C; Y—V—F—E—D—L—F—R; H—W—A—A—L—M—K—R;
M—P—E—D—F—Y—R—R; R—F—E—S—M—F—K—R; Y—W—E—A—H—V—R;
V—F—W—O—M—I—R—R; M—P—W—A—M—F—R—R; and S—F—M—D—M—F—K—R.

8. A method of claim 7, wherein the antiproliferative peptide is peptide K-P-W-W-V-S-R-V and the predetermined cell population is Sup B8.

9. A method of claim 1, wherein the anti-idiotype peptide sequence is less than 13 amino acids in length.

* * * * *